US010039886B2

(12) United States Patent
Pilkington et al.

(10) Patent No.: US 10,039,886 B2
(45) Date of Patent: Aug. 7, 2018

(54) SEALING ASSEMBLY FOR A SYRINGE BARREL

(71) Applicant: Black Tie Medical Inc., San Diego, CA (US)

(72) Inventors: Mary L. Pilkington, San Diego, CA (US); Mariano C. Riego de Dios, San Diego, CA (US)

(73) Assignee: Black Tie Medical Inc., San Diego, CA (US)

( * ) Notice: Subject to any disclaimer, the term of this patent is extended or adjusted under 35 U.S.C. 154(b) by 187 days.

(21) Appl. No.: 15/154,890

(22) Filed: May 13, 2016

(65) Prior Publication Data

US 2016/0367757 A1 Dec. 22, 2016

Related U.S. Application Data

(63) Continuation-in-part of application No. 14/846,357, filed on Sep. 4, 2015.

(60) Provisional application No. 62/162,367, filed on May 15, 2015, provisional application No. 62/162,389, filed on May 15, 2015.

(51) Int. Cl.
*A61M 5/315* (2006.01)
(52) U.S. Cl.
CPC .... *A61M 5/31513* (2013.01); *A61M 5/31511* (2013.01)
(58) Field of Classification Search
CPC .................. A61M 5/31513; A61M 5/31511
USPC ......................................................... 604/222
See application file for complete search history.

(56) References Cited

U.S. PATENT DOCUMENTS

| 5,002,538 A | 3/1991 | Johnson |
| 6,569,118 B2 | 5/2003 | Johnson et al. |
| 9,101,720 B2 * | 8/2015 | Okihara .............. A61M 5/1452 |
| 2016/0022917 A1 * | 1/2016 | Takai ................ A61M 5/31513 |
| | | 604/222 |

OTHER PUBLICATIONS

Tulip Product Catalog, select pages, Jan. 2014.
Alexander, Robert W., "Understanding Mechanical Emulsification Vs. Enzymatic Isolation of tSVF From Adipose Tissue", Journal of Prolotherapy, 8:e947-e960, Feb. 2016.
Tonnard, Patrick, et al., "Nanofat Grafting: Basic Research and Clinical Applications", Plastic and Reconstructive Surgery Journal, v. 132(4), at pp. 1017-1026, Oct. 2013.

* cited by examiner

*Primary Examiner* — Phillip Gray
(74) *Attorney, Agent, or Firm* — Rodney F. Brown

(57) ABSTRACT

A syringe sealing assembly includes a stopper coupling and a plunger coupling. The stopper coupling is adaptable to attach to a syringe stopper. The plunger coupling is releasably attachable to the stopper coupling. The stopper coupling is further adaptable to fit within a syringe barrel and to seal the interior of the syringe barrel from the external environment in cooperation with the syringe stopper. The plunger coupling is adaptable to attach to a syringe plunger. The plunger coupling is further adaptable to be received within a syringe barrel when the plunger coupling is attached to the stopper coupling. The plunger coupling is further adaptable to be withdrawn from the syringe barrel while the stopper coupling remains in the syringe barrel when the plunger coupling is detached from the stopper coupling.

20 Claims, 11 Drawing Sheets

SEALING ASSEMBLY FOR A SYRINGE BARREL

This a non-provisional patent application claiming the priority of Provisional Patent Application Ser. Nos. 62/162,367 and 62/162,389, both filed on May 15, 2015, which are incorporated herein by reference.

BACKGROUND OF THE INVENTION

The present invention relates generally to plastic surgery, more particularly to cosmetic surgery and still more particularly to fat transfer.

Fat transfer, also known as fat grafting, entails two procedures performed in series. In the first fat transfer procedure known as fat harvesting, fat is removed and recovered from one or more fatty sites on the body of a patient, such as the thighs or stomach, by any number of techniques including liposuction or lipoplasty. The harvested fat is a complex, multi-component mixture comprised of mature adipocytes, precursor adipocytes, other precursor cells and lipids from ruptured mature adipocytes. Adipocytes are the primary cells in adipose tissue, which is the loose connective tissue in the body where most fat resides. As connective tissue, adipose tissue also includes fibers and other non-fat material in addition to the adipocytes. Lipids are molecules including fat molecules which may be simplistically characterized as loose fat or fat particles. Harvested fat may be categorized by size as macrofat, microfat or nanofat in descending order of particle size.

In the second fat transfer procedure known as fat injection, the loose fat in the harvested fat is re-injected into the body of the same patient, but into one or more different sites on the body. The re-injected fat increases volume at the treated injection site and enhances the appearance of the patient. Potential injection sites include the face, breasts, cheeks, lips, buttocks, and chin.

Nanofat, as compared to larger fats, has been found to be more desirable for fat re-injection because it produces markedly better results in the ultimate appearance of the patient, particularly when treating superficial dermal layers such as eyelids and the like. Fat transfer practitioners have also found it highly advantageous to use very fine sharp syringe cannulas on the order of about 27-30 gauge when re-injecting harvested fat. The fine cannulas are less invasive and disruptive to the patient and can substantially reduce pain, bruising and/or other undesirable side effects of the procedure while simultaneously shortening patient recovery time. Nanofat, as compared to larger fats, does not substantially clog or otherwise impede flow through these very fine cannulas, thereby additionally rendering nanofat more desirable for fat re-injection. An exemplary fat transfer procedure using nanofat is described in "Nanofat Grafting: Basic Research and Clinical Applications," Tonnard, Patrick, et al., *Plastic and Reconstructive Surgery Journal*, v. 132(4), at pp. 1017-26, October 2013, which is incorporated herein by reference.

In view of the above, it has been found desirable to break down and size the harvested fat before re-injecting the fat into the body. One procedure for sizing harvested fat is centrifugation wherein the harvested fat is placed in a conventional centrifuge container such as a test tube and centrifuged. Centrifuging the harvested fat in the container desirably stratifies the harvested fat into discrete layers characterized by their density. The most dense material of the harvested fat resides in a most dense layer which settles to the bottom of the container. The least dense material of the harvested fat resides in a least dense layer which rises to the top of the container. The intermediate density material of the harvested resides in an intermediate density layer which is positioned intermediately between the most and least dense layers. It is often desirable to recover only one of these layers to the exclusion of the other layers for the subsequent fat injection procedure. For example, in some cases the intermediate density material has been found most desirable for the fat injection procedure. Unfortunately, it is often problematic to effectively recover the material of the intermediate density layer from the centrifuge container without contaminating this material with the material from the adjoining most and/or least dense layers.

The present invention recognizes a need for an apparatus and method which facilitates the stratification of harvested fat into more desirable material and less desirable material and which enables the practitioner to effectively and efficiently recover the desirable material from the harvested fat without contamination from the less desirable material while maintaining the system for stratification and recovery of the harvested fat anaerobic and closed to the external environment. Accordingly, it is an object of the present invention to provide an apparatus and method which satisfies the above needs. It is more generally an object of the present invention to provide an apparatus which enables the reconfiguration of a conventional syringe to a sealed fluid reservoir having utility, for example, as a sealed fluid storage and/or processing container. It is another general object of the present invention to provide a method for reconfiguring a conventional syringe to a sealed fluid reservoir having utility, for example, as a sealed fluid storage and/or processing container. It is more particularly an object of the present invention to provide an apparatus which enables the reconfiguration of a conventional syringe to a sealed fat processing container and, more particularly still, to a sealed centrifuge container. It is another more particular object of the present invention to provide a method for reconfiguring a conventional syringe to a sealed fat processing container and, more particularly still, to a sealed centrifuge container. These objects and others are accomplished in accordance with the invention described hereafter.

SUMMARY OF THE INVENTION

The present invention may be characterized as a syringe sealing assembly including a stopper coupling and a plunger coupling. The stopper coupling is adaptable to attach to a syringe stopper. In accordance with one embodiment, the stopper coupling is adaptable to be surroundingly retained within the syringe stopper, thereby effecting attachment of the stopper coupling to the syringe stopper. The plunger coupling is releasably attachable to the stopper coupling. In accordance with one embodiment, the plunger coupling and stopper coupling are releasably attachable to one another by a first cooperative threaded coupler on the stopper coupling and a second cooperative threaded coupler on the plunger coupling. The first cooperative threaded coupler may preferably be a female threaded bore and the second cooperative threaded coupler may preferably be a male threaded post. In accordance with one embodiment, the stopper coupling has a continuous passageway extending therethrough when the first cooperative threaded coupler is unscrewed from the second cooperative threaded coupler.

The stopper coupling is further adaptable to fit within a syringe barrel and to seal the interior of the syringe barrel from the external environment in cooperation with the syringe stopper. The plunger coupling is adaptable to attach to a syringe plunger. In accordance with one embodiment, the plunger coupling has a plunger bracket with an opening entering into an interior void space, wherein the opening and the interior void space are adaptable to receive and retain the syringe plunger in attachment to the plunger coupling. The plunger coupling is further adaptable to be received within a syringe barrel when the plunger coupling is attached to the stopper coupling. In accordance with one embodiment, the plunger coupling has a rotation stop adaptable to engage the syringe plunger when attached to the plunger coupling to prevent rotation of the plunger coupling independent of the syringe plunger while enabling rotation of the plunger coupling relative to the stopper coupling. The plunger coupling is further adaptable to be withdrawn from the syringe barrel while the stopper coupling remains in the syringe barrel when the plunger coupling is detached from the stopper coupling.

The present invention may be alternately characterized as a method which utilizes a syringe. The method attaches a stopper coupling of a sealing assembly to a syringe stopper and attaches a plunger coupling of a sealing assembly to a first end of a syringe plunger. The syringe stopper, stopper coupling, plunger coupling and first end of the syringe plunger are inserted into an interior of a syringe barrel via a first end of the syringe barrel. The first end, a second end and a sidewall of the syringe barrel bound the interior of the syringe barrel. The stopper coupling is releasably attached to the plunger coupling, such that the syringe barrel with the syringe stopper, stopper coupling, plunger coupling and syringe plunger therein comprises an operable syringe fitted with the sealing assembly. The syringe stopper, in cooperation with the stopper coupling, seals a sealed portion of the interior of the syringe barrel between the syringe stopper and the second end of the syringe barrel from the external environment of the syringe barrel.

In accordance with one embodiment, the method also detaches the plunger coupling from the stopper coupling while the stopper coupling is in the interior of the syringe barrel. The plunger coupling and syringe plunger are withdrawn in their entirety from the syringe barrel while maintaining the syringe stopper and the stopper coupling attached thereto in the syringe barrel. The resulting syringe barrel with the syringe stopper and stopper coupling therein comprises a fluid reservoir which still maintains the sealed portion of the interior of the syringe barrel. The fluid reservoir may preferably be used as a sealed centrifuge container that holds a fluid while the fluid is being centrifuged.

In accordance with one embodiment, the stopper coupling has a passageway extending therethrough. A fluid contained within the sealed portion is withdrawn from the fluid reservoir by inserting a syringe cannula connected to a second syringe barrel through the passageway and the syringe stopper into the fluid within the sealed portion and drawing the fluid through the cannula into the second syringe barrel. The fluid may preferably be a harvested fat. More particular, the fluid may preferably be from a stratum of a harvested fat bounded on one side within the sealed portion by a stratum of a different density harvested fat. The harvested fat drawn into the second syringe barrel may be essentially free of the different density harvested fat.

The invention will be further understood from the drawings and the following detailed description.

BRIEF DESCRIPTION OF THE SEVERAL VIEWS OF THE DRAWINGS

The below-listed drawing figures illustrate one or more embodiments of the present invention by way of example and not by way of limitation. Common reference characters may be used among the different drawing figures to indicate the same or similar structural elements.

DETAILED DESCRIPTION OF THE INVENTION

Figure 1:
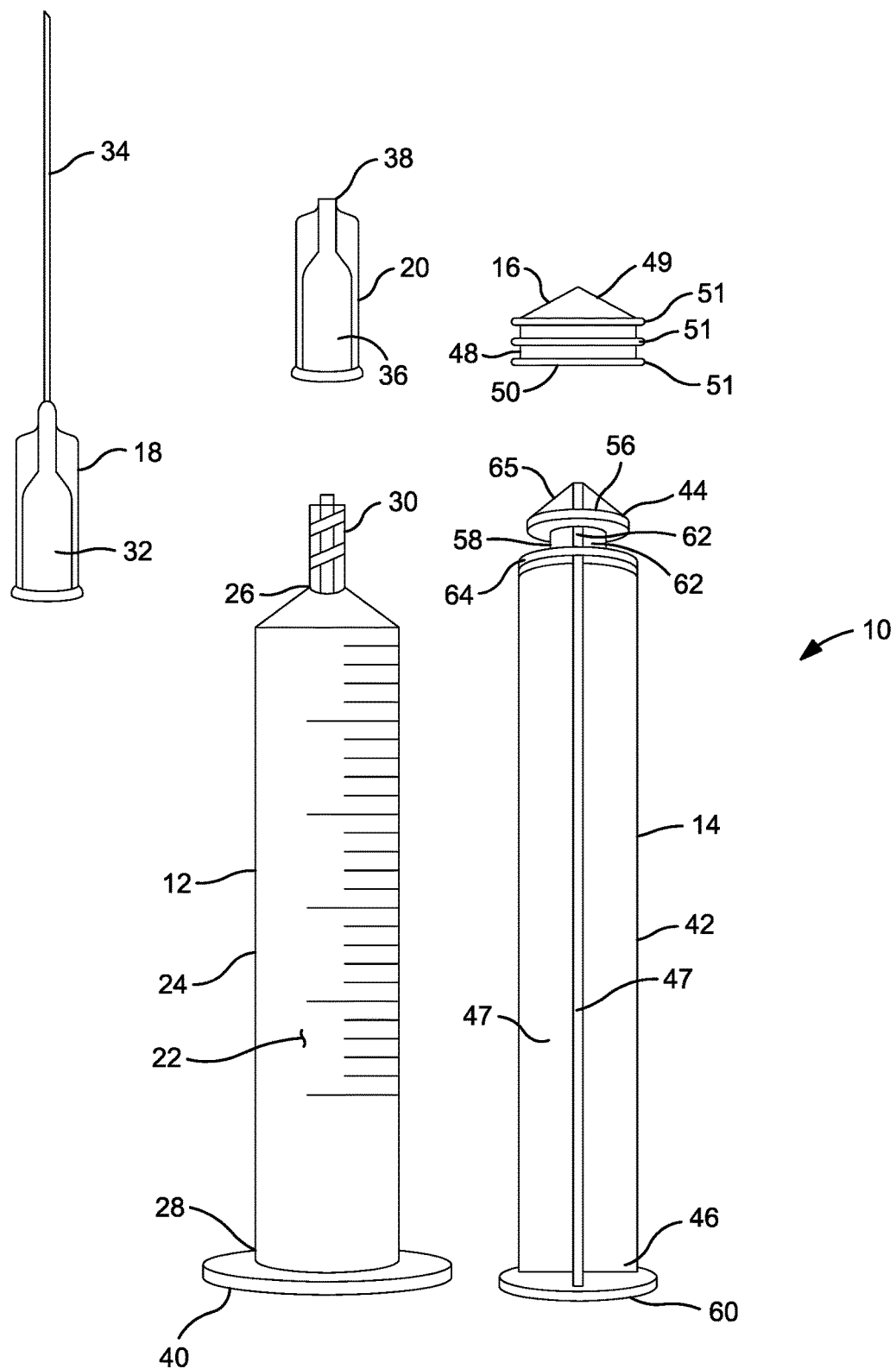
FIG. 1 shows the disassembled components of a conventional syringe which is adaptable for use with an embodiment of a sealing assembly.
Figure 2:
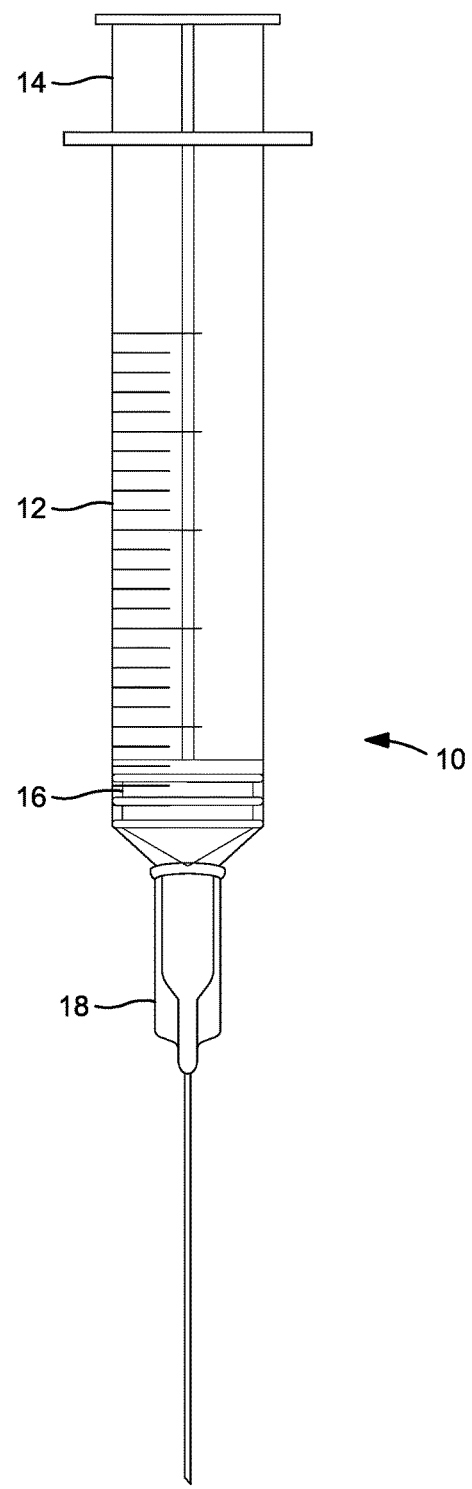
FIG. 2 is an elevation view of the assembled syringe of FIG. 1 having a dispensing tip fitted thereon.
Figure 3:
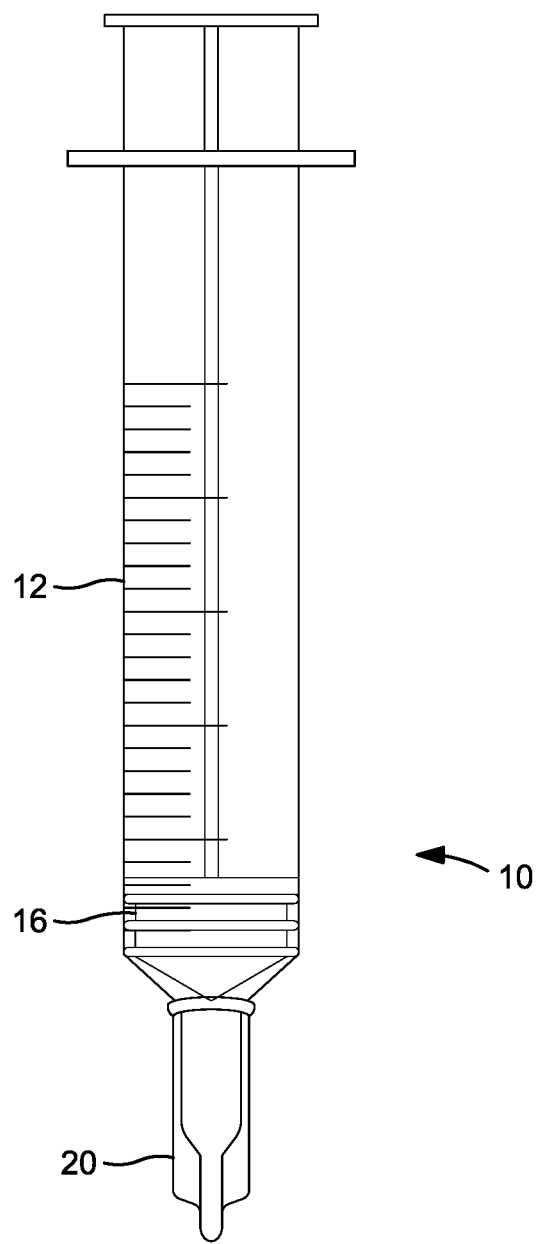
FIG. 3 is an elevation view of the assembled syringe of FIG. 1 having a closed cap fitted thereon.
Figure 4:
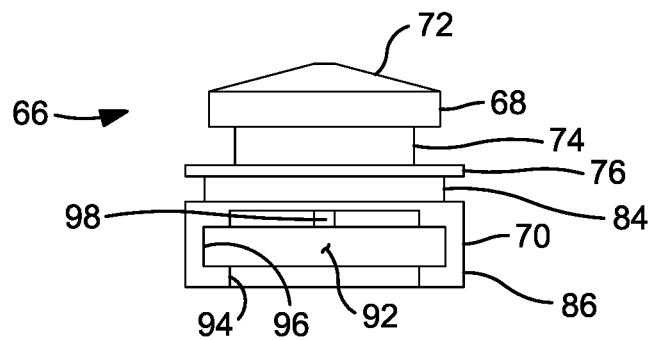
FIG. 4 is a front elevation view of an embodiment of a sealing assembly.

A conventional syringe is described with initial reference to FIGS. 1-3, which is generally designated 10. The syringe is preferably an off-the-shelf, sterile, disposable, single-use syringe including a barrel 12, a plunger 14, a stopper 16, a dispensing tip 18 and a cap 20. The barrel 12 is preferably a hollowed out cylinder formed in its entirety from a disposable transparent or translucent rigid plastic. The barrel 12 has an open interior 22 bounded by a continuous tubular side wall 24, a first end 26 and an opposite second end 28. The interior 22 defines a fluid retention chamber with a volume which is selectively adjustable in a manner described hereafter. The first end 26 is integrally fitted with a connection member 30, preferably in the form of a Luer coupler, a conventional fluid-tight connector fitting known for other medical applications, which extends across the first end 26. The integral connection member 30 enables a user to selectively transition the syringe 10 between a dynamic or active mode and a static or passive mode depending on whether the user removably attaches the dispensing tip 18 to the connection member 30 as shown in FIG. 2 or removably attaches the cap 20 to the connection member 30 as shown in FIG. 3.

The dispensing tip 18 has a Luer coupler 32 on one end and a cannula 34 on its opposite end which are substantially permanently, serially attached to one another. When the syringe 10 is configured with the dispensing tip 18 releasably attached to the connection member 30 of the barrel 12 by means of their respective Luer couplers, the dispensing tip 18 in cooperation with the connection member 30 provides fluid communication between the interior 22 of the barrel 12 and the external environment across the first end 26 of the barrel 12. The dispensing tip 18 in cooperation with the connection member 30 and in further cooperation with the plunger 14 enables the user to selectively charge fluid into the barrel 12 from the exterior of the syringe 10 or to discharge fluid from the barrel 12 into the exterior of the syringe 10 in a manner described hereafter. The cap 20 likewise has a Luer coupler 36 on its first end, but its opposite second end 38 is fully enclosed and sealed fluid tight. Therefore, when the syringe 10 is configured with the cap 20, rather than the dispensing tip 18, releasably attached to the connection member 30 of the barrel 12 by means of their respective Luer couplers, the cap 20 substantially prevents fluid communication between the interior 22 of the barrel 12 and the external environment across the first end 26 of the barrel 12.

The second end 28 of the barrel 12 is substantially open across the entire diameter of the interior 22 at the second end 28. A finger hold 40 having a disk configuration with a wider diameter than the barrel 12 is integrally formed with the outside edge of the second end 28 of the barrel 12. The finger hold 40 which facilitates gripping and operating the syringe 10 in a manner described hereafter.

The plunger 14 has an elongate shape and is also preferably formed in its entirety from a disposable rigid plastic. The plunger 14 has a main body 42, a first end 44 and a second end 46 which is opposite the first end 44. The main body 42 is constructed from two crisscrossed fins 47 which extend from the finger hold 40. Each fin 47 is preferably disposed at 90° angles from the other. The first end 44 of the plunger 14 is termed an inner end because it is received in the open second end 28 of the barrel 12 of the assembled syringe 10 shown in FIGS. 2 and 3 and extends into the interior 22 of the barrel 12.

Figure 5:
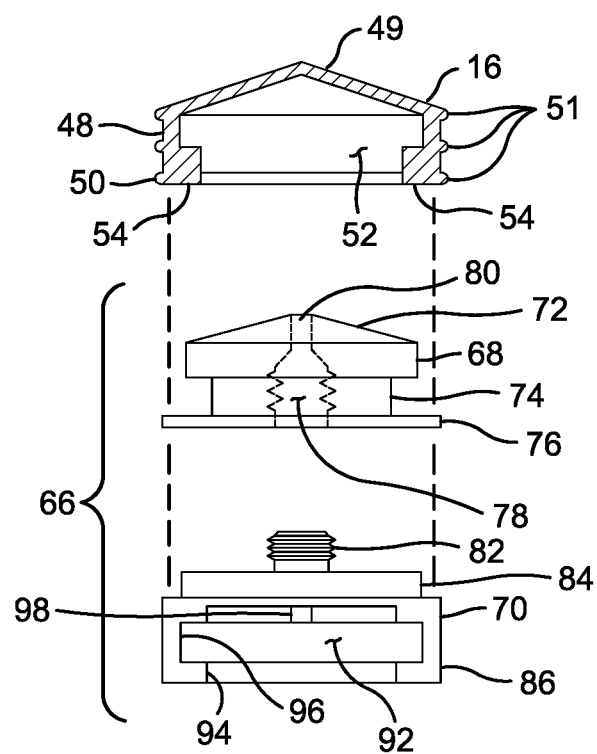
FIG. 5 is an exploded front view of the sealing assembly of FIG. 4 and a cross-section of an associated syringe stopper taken along its central longitudinal plane.
Figure 6:
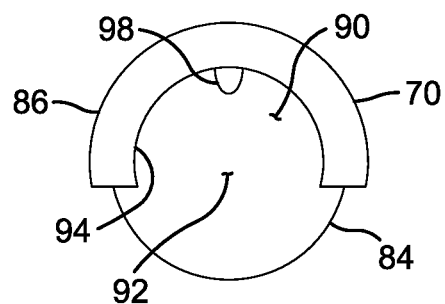
FIG. 6 is a bottom plan view of a plunger coupling employed in the sealing assembly of FIG. 4.
Figure 7:
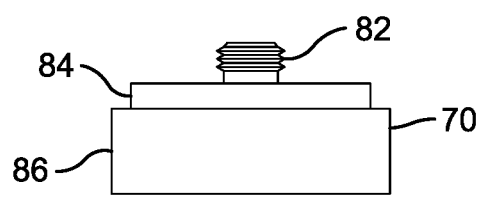
FIG. 7 is a rear elevation view of the plunger coupling of FIG. 6.
Figure 8:
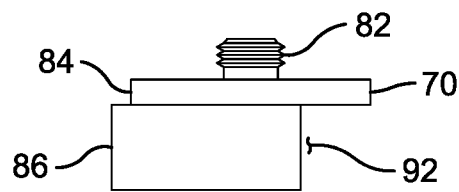
FIG. 8 is a side elevation view of a plunger coupling of FIG. 6.
Figure 9:
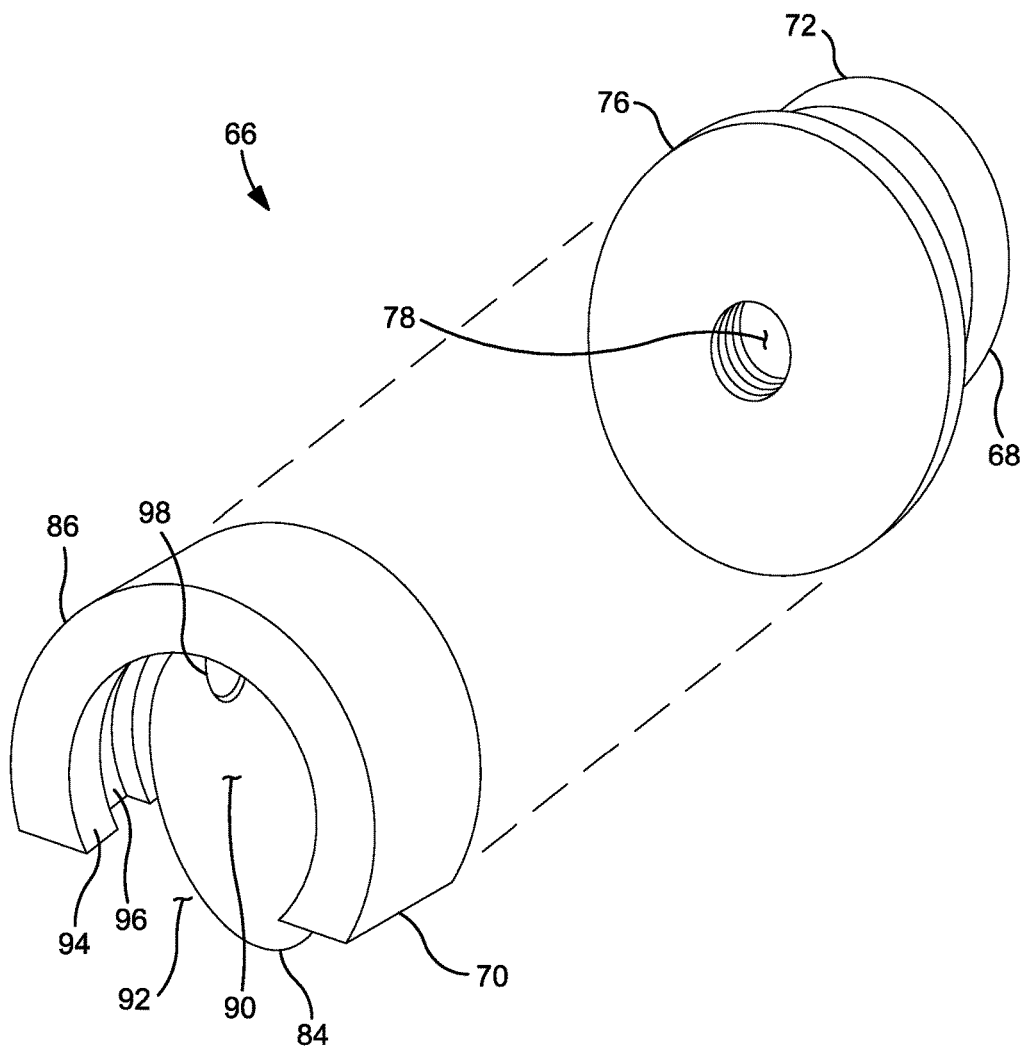
FIG. 9 is a bottom exploded perspective view of the sealing assembly of FIG. 4.
Figure 10:
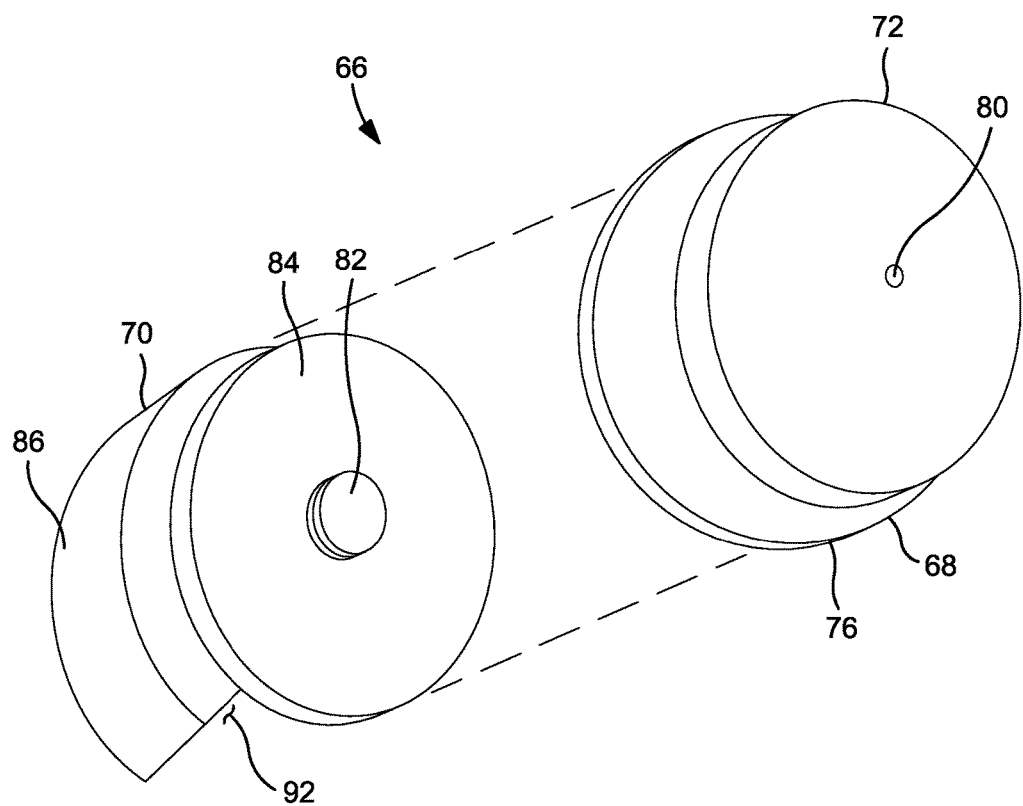
FIG. 10 is a top exploded perspective view of the sealing assembly of FIG. 4.

The stopper 16 is removably attached to the inner end 44 of the plunger 14 and substantially covers and encloses it in a manner described hereafter. As such, the inner end 44 of the plunger 14 functions as a stopper coupling in the conventional syringe 10. Referring specifically to FIGS. 1 and 5, the stopper 16 is a unitary structure configured in the shape of a hollowed-out cylindrical plug with a continuous tubular outer sidewall 48, a peaked conical-shaped first end 49 and an opposite open circular second end 50. The stopper 16 is preferably formed from a compressible elastic material such as rubber, synthetic rubber or other like elastomeric material. The outer sidewall 48 of the stopper 16 is preferably provided with a plurality of spaced-apart circumferential ribs 51 which extend outwardly therefrom.

The first end 49 of the stopper 16 is closed and the second end 50 opens into a retention chamber 52 in the interior of the stopper 16. The inside shape of the retention chamber 52 substantially conforms to the outer peripheral shape of the stopper 16. As such, the retention chamber 52 has a peaked conical-shaped first end, an opposite open circular second end and a continuous tubular inner sidewall. The stopper 16 has a retention lip 54 around the circumferential edge of the open second end 50. The inside diameter of the retention lip 54 is preferably substantially less than the diameter of the inner sidewall of the retention chamber 52.

The inner end 44 of the plunger 14 has an integral two-tiered configuration. The first tier is a stopper engagement member 56 and the second tier is a mounting base 58. The stopper engagement member 56 preferably has a disk configuration with a fixed diameter which is preferably less than the width of the main body 42. The diameter of the stopper engagement member 56 is also preferably at least slightly less than the unstretched diameter of the retention chamber 52 and greater than the unstretched inside diameter of the retention lip 54 on the open second end 50 of the stopper 16.

The stopper 16 is selectively removably attached to the inner end 44 of the plunger 14 by elastically stretching the retention lip 54 of the stopper 16 until the stretched inside diameter of the retention lip 54 is greater than the fixed diameter of the stopper engagement member 56. The user extends the stopper engagement member 56 past the stretched retention lip 54 into the retention chamber 52 of the stopper 16 until the stopper engagement member 56 is fully enclosed within the retention chamber 52. The user then releases the retention lip 54 and the retention lip 54 elastically returns to its unstretched inside diameter which is less than the fixed diameter of the stopper engagement member 56, thereby removably retaining the stopper 16 on the inner end 44 of the plunger 14. The stopper 16 is selectively removed from the inner end 44 of the plunger 14 by again elastically stretching the retention lip 54 of the stopper 16 until the stretched inside diameter of the retention lip 54 is greater than the diameter of the stopper engagement member 56. The user then withdraws the stopper engagement member 56 past the stretched retention lip 54 and out of the retention chamber 52.

The diameter of the outer sidewall 48 of the stopper 16 and the width of the main body 42 of the plunger 14 are preferably substantially equal to one another. The diameter of the outer sidewall 48 of the stopper 16 and the width of the main body 42 of the plunger 14 are also each preferably about equal to the inside diameter of the barrel 12, i.e., the diameter of the interior 22 of the barrel 12. In the present case "about equal to" means that the diameter of the outer sidewall 48 of the stopper 16 and the width of the main body 42 of the plunger 14 are only very slightly smaller than the diameter of the interior 22 of the barrel 12. In contrast, the outside diameters of the compressible ribs 51 of the stopper 16 are preferably slightly greater than the diameter of the interior 22 of the barrel 16 when the ribs 51 are uncompressed. Accordingly, the plunger 14 and stopper 16 nest snugly within the interior 22 of the barrel 12, but are still slidably displaceable therein relative to the barrel 12 when a manual pushing or pulling force is applied to the plunger 14. The slightly oversize fit of the compressible ribs 51 in the interior 22 of the barrel 12 provides a fluid tight seal between the outside edge of the stopper 16 and the sidewall 24 of the barrel 12.

The plunger 14 and stopper 16 in combination preferably have a length greater than the length of the interior 22 of the barrel 12 so that the second end 46 of the plunger 14 extends out of the open second end 28 of the barrel 12 when the plunger 14 is fully depressed into the interior 22 with the stopper 16 abutting the first end 26 of the barrel 12. A finger hold 60 having a disk configuration with a wider diameter than the main body 24 of the plunger 14 is integrally formed with the second end 46 of the plunger 14. The finger hold 60 facilitates gripping and operating the syringe 10 and, more particularly, facilitates displacing the plunger 14 and stopper 16 in a first direction away from the first end 26 of the barrel 12 by manually pulling on the finger hold 60. The finger hold 60 also facilitates displacing the plunger 14 and stopper 16 in an opposite second direction toward the first end 26 of the barrel 12 by manually pushing on the finger hold 60.

It is readily apparent that when the stopper 16 and plunger 14 are displaced in the first direction, they act in the manner of a piston and a variable-volume fluid retention chamber is formed in the interior 22 of the barrel 12 between the first end 26 of the barrel 12 and the stopper 16. The variable-volume fluid retention chamber increases in volume as the degree of displacement in the first direction increases. Thus, pulling on the plunger 14 enables the user to draw fluid into the barrel 12 of the syringe 10. It is further apparent that when the stopper 16 and plunger 14 are displaced in the second direction, the variable-volume fluid retention chamber decreases in volume as the degree of displacement in the second direction increases. Thus, depressing, i.e., pushing on, the plunger 14 enables the user to evacuate fluid from the barrel 12 of the syringe 10.

Referring specifically to FIG. 1, the mounting base 58 preferably permanently connects the stopper engagement member 56 and the main body 42 of the plunger 14 to one another. The mounting base 58 is integrally positioned between the stopper engagement member 56 and the main body 42 of the plunger 14 and has substantially the same configuration as the main body 42 with crisscrossed fins 62 extending from a disk-shaped mount 64. One end of the fins 62 merges into the mount 64 and the other end of the fins 62 merges into the stopper engagement member 56. The diameter of the mount 64 is preferably substantially equal to the width of the main body 42 and the width of the aligned fins 62 in combination is preferably less than the diameter of the stopper engagement member 56. The stopper engagement member 56 includes a two-finned crest 65 on the side opposite the fins 62 which has a width substantially equal to the diameter of the stopper engagement member 56. The outer peripheral shape of the crest 65 substantially conforms to the peaked conical shape of the first end of the retention chamber 52.

An embodiment of a sealing assembly is described hereafter with reference to FIGS. 4-10. The sealing assembly is generally designated 66 and is comprised of a stopper coupling 68 and a plunger coupling 70 which are selectively attachable to or detachable from one another. The sealing assembly 66 is preferably formed in its entirety from one or more materials, such as metal or plastic, which are generally characterized as durable, strong, rigid, wear-resistant, non-corrosive, smooth, non-porous, substantially inert and having a surface which does not readily retain contaminants. The materials of the sealing assembly 66 having the above-recited characteristics may either be sterile, disposable, single-use materials similar to those of the syringe 10 or may be heat-resistant reusable materials which are suitable for autoclaving.

Figure 11:
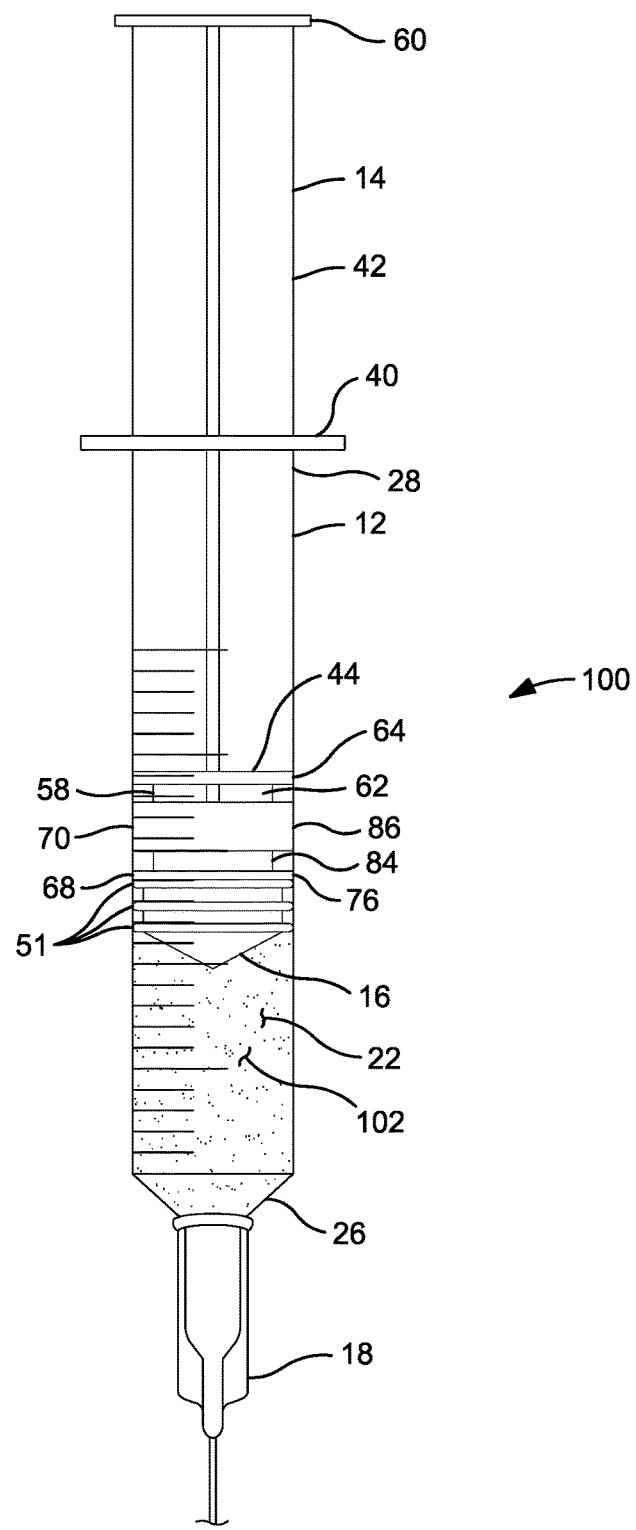
FIG. 11 is an elevation view of a syringe having the sealing assembly of FIG. 4 fitted therein.
Figure 12:
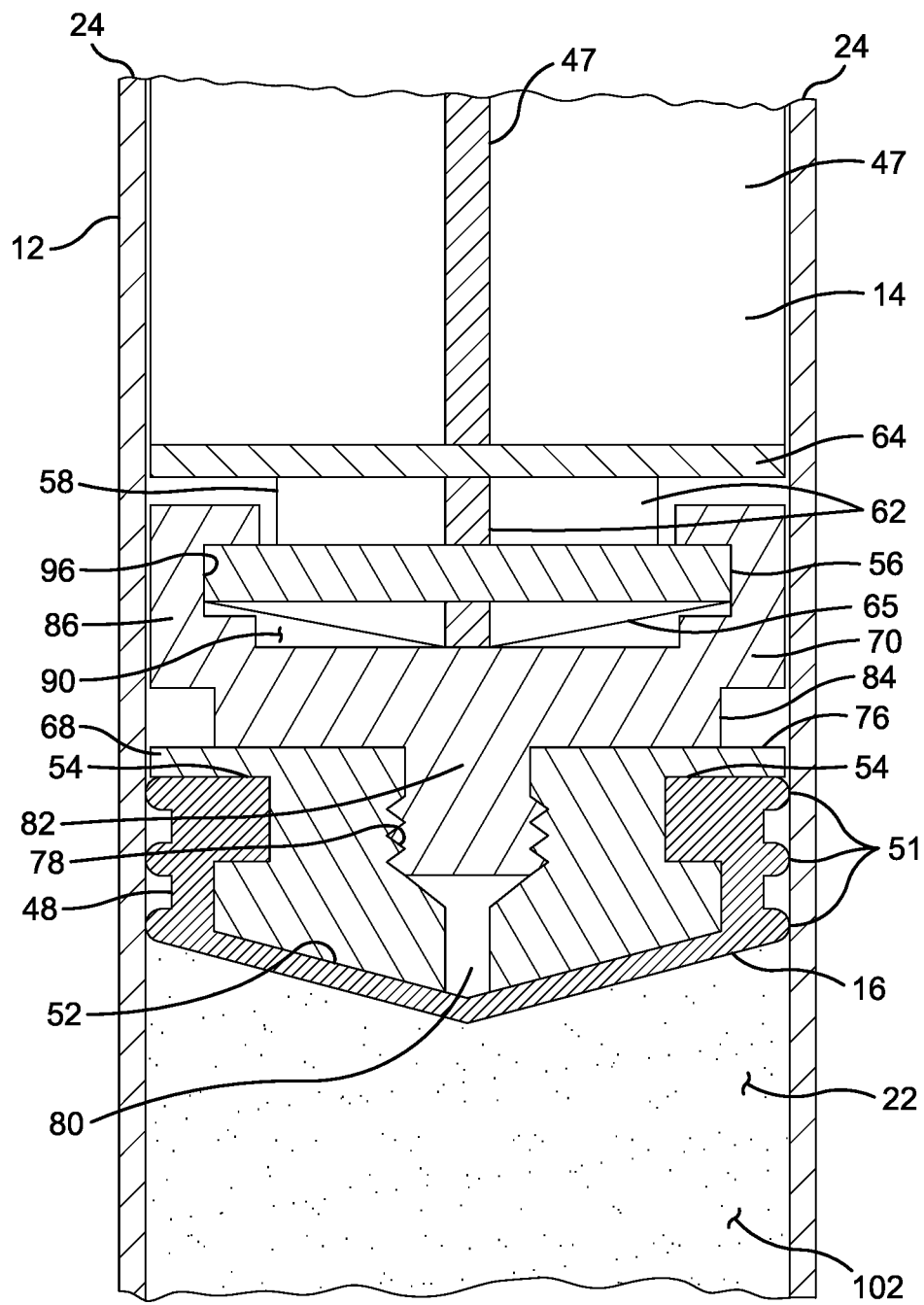
FIG. 12 is a close-up cross-section of the syringe and sealing assembly of FIG. 11 taken along their central longitudinal plane.

The stopper coupling 68 preferably has a unitary construction which includes a stopper retention cap 72, a connector segment 74 and a plunger coupling interface 76 integrally formed with one another in series such that the connector segment 74 extends between the stopper retention cap 72 on one side of the stopper coupling 68 and the plunger coupling interface 76 on the other side of the stopper coupling 68. The stopper retention cap 72 is sized and configured to be received and releasably retained in the retention chamber 52 of the stopper 16 in place of the stopper engagement member 56 of the plunger 14 when a syringe is newly assembled or retrofitted with the present sealing assembly 66 as shown in FIGS. 11 and 12. As such, the outer peripheral shape of the stopper retention cap 72 substantially conforms to the inside shape of the retention chamber 52. Placement and releasable retention of the stopper retention cap 72 in the retention chamber 52 is effected in substantially the same manner as placement and retention of the stopper engagement member 56 in the retention chamber 52 described above.

The plunger coupling interface 76 is preferably configured as a planar disk or circular plate. The connector segment 74 is preferably configured as a cylinder with a first end and a second end opposite the first end. The longitudinal axis of the stopper coupling 68 coincides with central cylindrical axes of the stopper retention cap 72, connector segment 74 and plunger coupling interface 76 and is substantially perpendicular to the plane of the plunger coupling interface 76. A first cooperative coupler 78 in the form of a female threaded bore extends from one end of the stopper coupling 68 along the longitudinal axis thereof through the entirety of the plunger coupling interface 76 and connector segment 74 and into the stopper retention cap 72. A smaller cannula aperture 80 serially aligns with the first cooperative coupler 78 and extends along the longitudinal axis through the remainder of the stopper retention cap 72 to the other end of the stopper coupling 68.

The plunger coupling 70 preferably has a unitary construction which includes a second cooperative coupler 82, a stopper coupling interface 84 and a plunger retention bracket 86 integrally formed with one another in series such that the stopper coupling interface 84 extends between the second cooperative coupler 82 on one end of the plunger coupling 70 to the plunger retention bracket 86 on the other end of the coupling 68. The stopper coupling interface 84 is preferably configured as a planar disk or circular plate. The second cooperative coupler 82 extends from one side of the stopper coupling interface 84 and has a narrow cylindrical post configuration with male threads formed on its longitudinal circumferential surface. The cylindrical axis of the second cooperative coupler 82 is perpendicularly aligned with the diameter of the plunger coupling interface 84. The second cooperative coupler 82 is sized to be threadably received in the first cooperative coupler 78 of the stopper coupling 68 and releasably retained therein.

The plunger retention bracket 86 extends from the opposing second side of the stopper coupling interface 84. The plunger retention bracket 86 is an arcuate wall having a partial tubular configuration which extends around about 0.6 of the entire circumference of the adjacent stopper coupling interface 84. As a result, a radial cross-section of the plunger retention bracket 86 is approximately horseshoe shaped. The interior of the plunger retention bracket 86 is an open void space 90 which is accessible from the outside through an opening 92 left by an omitted segment in the circumferential wall that is the plunger retention bracket 86. The width of the opening 92 is about equal to the diameter of the stopper engagement member 56 so that the stopper engagement member 56 passes tightly through the opening 92 into the interior void space 90. The plunger retention bracket 86 has an inside face 94 with a circumferential slot 96 formed therein which is continuous along the extent of the inside face 94. The diameter of the circumferential slot 96 is about equal to the diameter of the stopper engagement member 56 so that the circumferential edge of the stopper engagement member 56 fits snugly within the circumferential slot 96. As such, the void space 90, opening 92 and circumferential slot 96 are sized and configured to receive and releasebly retain the stopper engagement member 56 therein when a syringe is newly assembled or retrofitted with the present sealing assembly 66 in a manner described below.

A rotation stop 98 may also be integrally formed on the inside face 94 of the plunger retention bracket 86 or elsewhere on the plunger coupling 70 to substantially prevent independent rotation of the plunger coupling 70 relative to the plunger 14. The rotation stop 98 of the plunger coupling 70 preferably engages the inner end 44 of the plunger 14 when the sealing assembly 66 is fitted in a syringe as described hereafter and shown in FIG. 12, thereby enabling the plunger 14 and plunger coupling 70 to rotate in unison within the interior 22 of the barrel 12 and preventing either the plunger 14 or the plunger coupling 70 from rotating independent of the other.

Methods for fitting a syringe with the above-described sealing assembly 66 and for using the resulting syringe with the sealing assembly 66 fitted therein are described hereafter with continuing reference to FIGS. 4-10 and additional reference to FIGS. 1 and 11-14. In accordance with one embodiment, a method for fitting a syringe with the sealing assembly 66 is a retrofit method, wherein the plunger 14 is initially completely withdrawn from the interior 22 of the barrel 12 of the conventional syringe 10 and the stopper 16 is removed from the inner end 44 of the plunger 14 in a manner described above. The exposed stopper engagement member 56 including the crest 65 on the inner end 44 of the plunger 14 is press-fitted through the undersized opening 92 in the plunger retention bracket 86 and press-fitted into the tight-fitting void space 90 and circumferential slot 96 where it is releasably retained. The stopper coupling 68 and plunger coupling 70 are also releasably attached to one another by threading the second cooperative coupler 82 of the plunger coupling 70 into the first cooperative coupler 78 of the stopper coupling 68. The stopper 16 is then fitted over of the stopper coupling 68 and releasably retained thereon in substantially the same manner as described above with respect to the stopper 16 and the inner end 44 of the plunger 14 of the conventional syringe 10. The stopper retention cap 72 is snugly retained in the retention chamber 52 by means of the retention lip 54 on the inside edge of the stopper 16. The plunger 14 having the sealing assembly 66 mounted on its inner end 44 is then returned to the interior 22 of the barrel 12.

As an alternative to retrofitting, a syringe can be fitted with the sealing assembly 66 as original equipment during manufacturing of the syringe. A preferred method for fitting a syringe with the sealing assembly 66 as original equipment is essentially the same as described above with respect to the retrofit method except that the stopper engagement member 56 is already exposed at the time that the present original equipment method is initiated.

In any case, the resulting syringe having the sealing assembly 66 fitted therein is shown in FIGS. 11 and 12 and generally designated 100. Elements of the syringe 100 which are common to the conventional syringe 10 are designated by the same reference characters as used in FIGS. 1-3. The syringe 100 can be utilized in a conventional manner for all customary syringe functions including the withdrawal of fluid from a fluid source or the injection of fluid into a fluid receiver. It is noted that the presence of the sealing assembly 66 does not impair conventional operation of the syringe 100. Thus, for example, the practitioner can use the syringe 100 in a conventional manner to withdraw harvested fat from the body of a patient or from an alternate harvested fat storage reservoir and can additionally or alternately use the syringe 100 for injection of harvested fat into a body of a patient. As such, FIGS. 11 and 12 show the barrel 12 of the syringe containing a fluid 102 such as a harvested fat.

Figure 13:
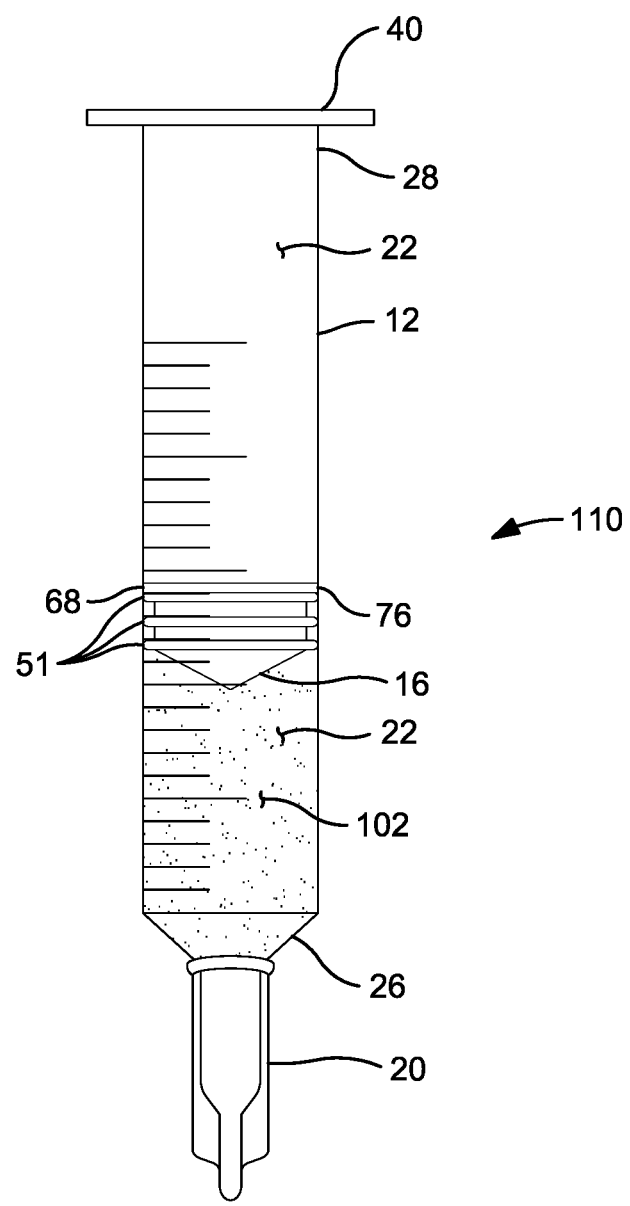
FIG. 13 is an elevation view of a syringe and the sealing assembly of FIG. 4 adapted for use as a sealed fluid reservoir.
Figure 14:
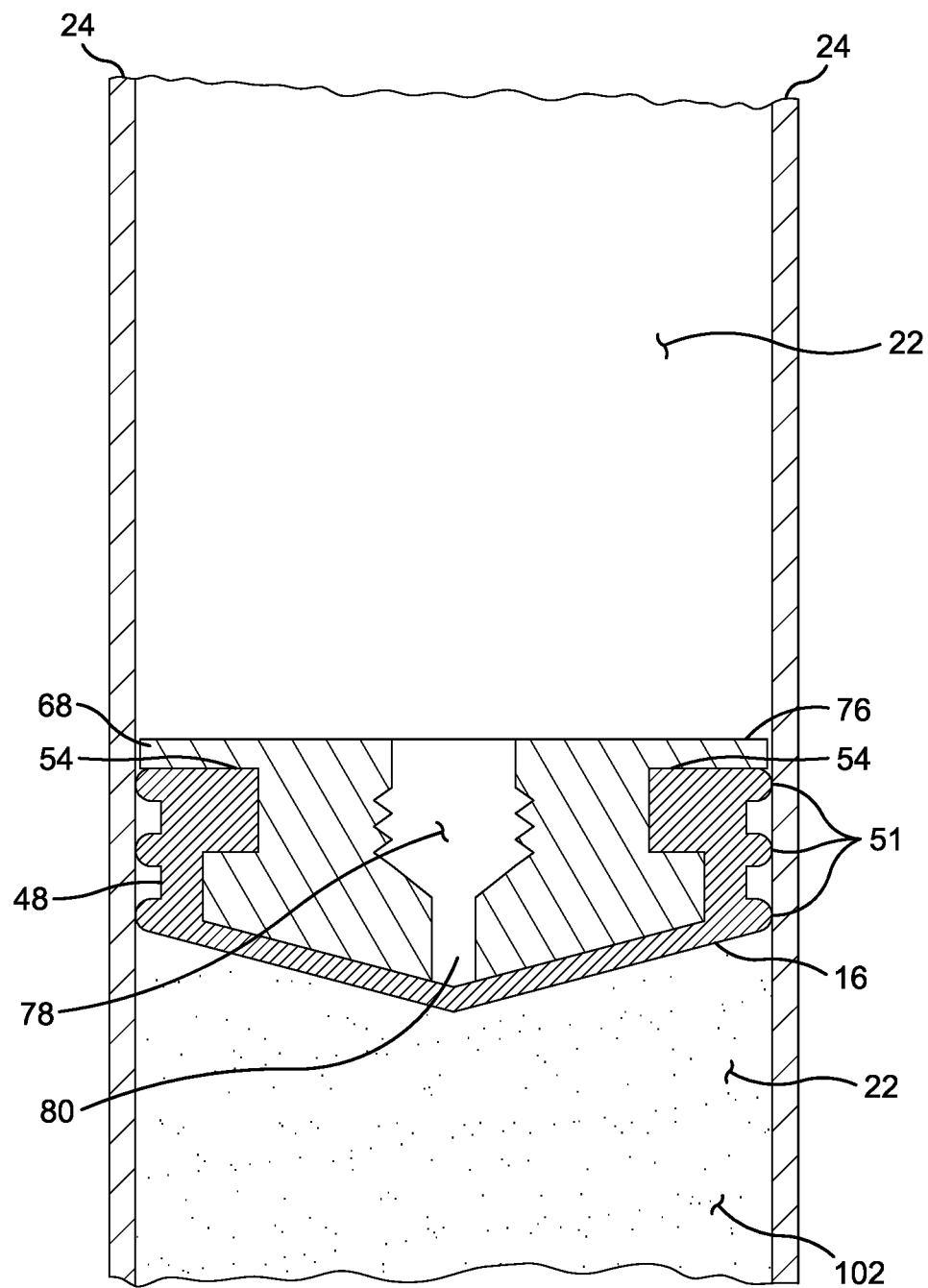
FIG. 14 is a close-up cross-section of the sealed fluid reservoir of FIG. 13 taken along their central longitudinal plane.

If it is desired to store or otherwise process the fluid 102 contained in the barrel 12, the syringe 100 can be reconfigured to a sealed fluid reservoir as shown in FIGS. 13 and 14, wherein the sealed fluid reservoir is generally designated 110. Elements of the sealed fluid reservoir 110 which are common to the conventional syringe 10 or the syringe 100 are designated by the same reference characters as used in FIGS. 1-3 or FIGS. 11 and 12, respectively. The sealed fluid reservoir 110 has utility as a sealed fluid storage container or a sealed fluid processing container. More particularly, the sealed fluid reservoir 110 has utility as a sealed fat processing container and, more particularly still, as a sealed centrifuge container.

To reconfigure the syringe 100 to a sealed fluid reservoir 110, the practitioner removes the dispensing tip 18 from the connection member 30 on the first end 26 of the syringe 100 which contains the fluid 102 in the syringe barrel 12 and replaces the dispensing tip 18 with the closed cap 20. The practitioner grasps the finger hold 60 of the syringe plunger 14 and uses it to manually rotate the plunger 14. The plunger coupling 70, which is attached to plunger 14 in the syringe barrel 12, rotates in correspondence with the plunger 14 due to the rotation stop 98. It is noted that the stopper 16 and correspondingly the stopper coupling 68, which is attached to the stopper 16 in the syringe barrel 12, are both maintained stationary relative to the barrel 12 as the plunger 14 and plunger coupling 70 rotate. The plunger 14 and plunger coupling 70 are rotated in a direction which unscrews the second cooperative coupler 82 of the plunger coupling 70 from the first cooperative coupler 78 of the stopper coupling 68. Unscrewing the second cooperative coupler 82 from the first cooperative coupler 78 disengages the plunger coupling 70 and plunger 14 from the stopper coupling 68 and stopper 16 and enables the practitioner to withdraw the plunger coupling 70 and plunger 14 from the syringe barrel 12 in their entirety while maintaining the stopper 16 and stopper coupling 68 in their same position within the barrel 12 which results in the sealed fluid reservoir 110. It is apparent that the fluid 102 remains static and sealed within the barrel 12 throughout the present syringe reconfiguration method and is not exposed to the external environment outside of the syringe barrel 12.

The resulting sealed fluid reservoir 110 which omits the plunger 14 advantageously renders the sealed fluid reservoir 110 more compact than the syringes 10 or 100 and enables utilization of the sealed fluid reservoir as a fluid storage container or fluid processing container without interference from the plunger 14 while still maintaining the syringe barrel 12 with the fluid 102 contained therein sealed. It is apparent that the first cooperative coupler 78 and cannula aperture 80 in series define a continuous open passageway through the stopper coupling 68 along its central longitudinal axis when the second cooperative coupler 82 is disengaged from the first cooperative coupler 78. Therefore, the practitioner is able to access the fluid 102 in the barrel 12 once storage or processing of the fluid 102 retained in the barrel 12 is completed by inserting the cannula 34 from another syringe 10 or 100 through the first cooperative coupler 78 and cannula aperture 80 in the stopper coupling 68 and puncturing the stopper 16 with the cannula 34 so that the cannula 34 extends into the fluid 102. The fluid 102 can then be withdrawn through the cannula 34 into the other syringe 10 or 100.

Thus, for example, a practitioner is able use the syringe 100 to harvest fat from the body of a patient, convert the syringe 100 to the sealed fluid reservoir 110 and centrifuge the harvested fat using the sealed fluid reservoir 110 as the centrifuge container while the harvested fat remains sealed in the syringe barrel 12 throughout the entire process without risk of contamination or spillage. Once centrifugation of the harvested fat is completed, the practitioner is able to withdraw the harvested fat from any stratum in the barrel 12 by inserting the cannula 34 from another syringe 10 or 100 through the stopper coupling 68 and stopper 16 into the desired stratum of harvested fat, e.g., nanofat, in the barrel 12 and withdraw the harvested fat into the other syringe 10 or 100 which may then be used to re-inject the harvested fat into the same patient. It is apparent that the above-described method of use is preferably closed and anaerobic.

While the forgoing preferred embodiments of the invention have been described and shown, it is understood that alternatives and modifications, such as those suggested and others, may be made thereto and fall within the scope of the invention. For example, it is apparent that the present invention contemplates modifications to the specific embodiments of the sealing assembly taught herein and such modifications are within the purview of the skilled artisan and within scope of the invention.

We claim:

1. A syringe sealing assembly comprising:
   a stopper coupling including a first cooperative coupler, wherein said stopper coupling is adaptable to removably attach to a syringe stopper; and
   a plunger coupling including a second cooperative coupler and a plunger retention bracket, wherein said plunger coupling is releasably attachable to said stopper coupling by releasably coupling said first cooperative coupler with said second cooperative coupler, wherein said plunger retention bracket is an arcuate wall having a horseshoe-shaped configuration partially extending around an interior void space within said plunger retention bracket accessible from outside said plunger retention bracket through an opening in said arcuate wall, wherein said plunger retention bracket is adaptable to selectively attach to a syringe plunger by press-fitting the syringe plunger through said opening into said interior void space and retaining the syringe plunger in said interior void space and to selectively detach from the syringe plunger by withdrawing the syringe plunger through said opening out of said interior void space, wherein said stopper coupling is further adaptable to fit within a syringe barrel enclosed by a barrel sidewall and to seal the interior of the syringe barrel from the external environment in cooperation with the syringe stopper, and wherein said plunger coupling is further adaptable to be received within the syringe barrel with said arcuate wall of said plunger retention bracket parallely aligned with said barrel sidewall when said plunger coupling is attached to said stopper coupling and to be withdrawn from the syringe barrel while said stopper coupling remains in the syringe barrel when said plunger coupling is detached from said stopper coupling.

2. The syringe sealing assembly of claim 1, wherein said stopper coupling is rigid and the syringe stopper is elastic, wherein said stopper coupling includes a connector segment having a segment outer edge bounding a segment outside diameter and a stopper retention cap having a cap outer edge bounding a cap outside diameter greater than said segment outside diameter and stopper retention cap, wherein said connector segment is serially positioned adjacent to said stopper retention cap, wherein a stopper retention ledge extends between said cap outer edge and said segment outer edge, wherein said cap outside diameter is adaptable to be greater than an unstretched inside diameter of a stretchable retention lip of the syringe stopper extending around a perimeter of a retention chamber of the syringe stopper and said cap outside diameter is adaptable to be less than a stretched inside diameter of the stretchable retention lip, thereby rendering said stopper retention cap adaptable to be removably inserted past the stretchable retention lip having the stretched inside diameter into the retention chamber of the syringe stopper and, wherein said stopper retention cap is adaptable to be removably retained within the retention chamber by abutting the stretchable retention lip against said stopper retention ledge, thereby effecting removable attachment of said stopper coupling to the syringe stopper.

3. The syringe sealing assembly of claim 1, wherein said plunger retention bracket has a circumferential slot on an inside face of said arcuate wall, wherein said circumferential slot is adaptable to receive a disk-configured member of the syringe plunger perpendicularly aligned with said arcuate wall when the syringe plunger is retained in said interior void space, thereby facilitating selective attachment of said plunger retention bracket to the syringe plunger.

4. The syringe sealing assembly of claim 1, wherein said first cooperative coupler is a female threaded bore and said second cooperative coupler is a male threaded post.

5. The syringe sealing assembly of claim 1, wherein said stopper coupling has a continuous passageway extending therethrough when said first cooperative coupler is uncoupled from said second cooperative threaded coupler.

6. The syringe sealing assembly of claim 1, wherein said plunger coupling has a rotation stop adaptable to engage the syringe plunger when attached to said plunger coupling to prevent rotation of said plunger coupling independent of the syringe plunger while enabling rotation of said plunger coupling relative to said stopper coupling.

7. A syringe sealing assembly comprising:
   an elastic syringe stopper including a retention chamber and a stretchable retention lip extending around a perimeter of said retention chamber;
   a rigid stopper coupling removably coverable by said elastic syringe stopper, wherein said rigid stopper coupling includes a first cooperative coupler, a connector segment having a segment outer edge bounding a segment outside diameter and a stopper retention cap having a cap outer edge bounding a cap outside diameter greater than said segment outside diameter, wherein said connector segment is serially positioned adjacent to said stopper retention cap, wherein a stopper retention ledge extends between said cap outer edge and said segment outer edge, wherein said cap outside diameter is greater than an unstretched inside diameter of said stretchable retention lip and said cap outside diameter is less than a stretched inside diameter of said stretchable retention lip, thereby rendering said stopper retention cap removably insertable past said stretchable retention lip having said stretched inside diameter into said retention chamber, and wherein said stopper retention cap is removably retainable within said retention chamber by abutting said stretchable retention lip against said stopper retention ledge;
   a plunger coupling including a second cooperative coupler and a plunger retention bracket, wherein said plunger coupling is releasably attachable to said rigid stopper coupling by releasably coupling said first cooperative coupler with said second cooperative coupler, wherein said plunger retention bracket is an arcuate wall having a horseshoe-shaped configuration partially extending around an interior void space within said plunger retention bracket accessible from outside said plunger retention bracket through an opening in said arcuate wall, wherein said plunger retention bracket is adaptable to selectively attach to a syringe plunger by press-fitting the syringe plunger through said opening into said interior void space and retaining the syringe plunger in said interior void space and to selectively detach from the syringe plunger by withdrawing the syringe plunger through said opening out of said interior void space; and wherein said rigid stopper coupling is further adaptable to fit within a syringe barrel enclosed by a barrel sidewall and to seal the interior of the syringe barrel from the external environment in cooperation with said elastic syringe stopper, and wherein said plunger coupling is further adaptable to be received within the syringe barrel with said arcuate wall of said plunger retention bracket parallely aligned with the barrel sidewall when said plunger coupling is attached to said rigid stopper coupling and to be withdrawn from the syringe barrel while said rigid stopper coupling remains in the syringe barrel when said plunger coupling is detached from said rigid stopper coupling.

8. The syringe sealing assembly of claim 7, wherein said first cooperative coupler is a female threaded bore and said second cooperative coupler is a male threaded post.

9. The syringe sealing assembly of claim 7, wherein said rigid stopper coupling has a continuous passageway extending therethrough when said first cooperative coupler is uncoupled from said second cooperative coupler.

10. The syringe sealing assembly of claim 7, wherein said plunger coupling has a rotation stop adaptable to engage the syringe plunger when attached to the plunger coupling to prevent rotation of said plunger coupling independent of the syringe plunger while enabling rotation of said plunger coupling relative to said rigid stopper coupling.

11. A method utilizing a syringe comprising the steps of:
attaching a stopper coupling of a sealing assembly to a syringe stopper;
attaching a plunger coupling of a sealing assembly to a first end of a syringe plunger;
inserting said syringe stopper, said stopper coupling, said plunger coupling and said first end of said syringe plunger into an interior of a syringe barrel via a first end of said syringe barrel, wherein said first end, a second end and a sidewall of said syringe barrel bound said interior of said syringe barrel, and wherein said stopper coupling is releasably attached to said plunger coupling, such that said syringe barrel with said syringe stopper, said stopper coupling, said plunger coupling and said syringe plunger therein comprises an operable syringe fitted with said sealing assembly, wherein said syringe stopper in cooperation with said stopper coupling seals a sealed portion of said interior of said syringe barrel between syringe stopper and said second end of said syringe barrel from the external environment of said syringe barrel;
detaching said plunger coupling from said stopper coupling while said stopper coupling is in said interior of said syringe barrel; and
withdrawing said plunger coupling and said syringe plunger in their entirety from said syringe barrel while maintaining said syringe stopper and said stopper coupling attached thereto in said syringe barrel such that said syringe barrel with said syringe stopper and said stopper coupling therein comprises a fluid reservoir, wherein said fluid reservoir maintains said sealed portion of said interior of said syringe barrel and is used as a sealed centrifuge container that holds a fluid while said fluid is being centrifuged.

12. The method of claim 11, wherein said stopper coupling has a continuous passageway extending therethrough, said method further comprising withdrawing a centrifuged fluid contained within said sealed portion from said fluid reservoir by inserting a syringe cannula connected to a second syringe barrel through said passageway and said syringe stopper into said fluid within said sealed portion and drawing said fluid through said cannula into said second syringe barrel.

13. The method of claim 11, wherein said fluid is a harvested fat.

14. The method of claim 12, wherein said centrifuged fluid is from a stratum of a harvested fat bounded on one side within said sealed portion by a stratum of a different density harvested fat.

15. The method of claim 14, wherein said harvested fat drawn into said second syringe barrel is essentially free of said different density harvested fat.

16. A method utilizing a syringe comprising the steps of:
a rigid stopper coupling has a stopper retention cap and a segment connector serially positioned adjacent to said stopper retention cap and the stopper retention cap is removably covered with an elastic syringe stopper by stretching a stretchable retention lip extending around a perimeter of a retention chamber of said elastic syringe stopper so that said stretchable retention lip has a stretched inside diameter exceeding a cap outside diameter of said stopper retention cap, removably inserting said stopper retention cap past said stretchable retention lip having said stretched inside diameter into said retention chamber and retaining said stopper retention cap in said retention chamber by abutting said stretchable retention lip against a stopper retention ledge positioned at an intersection of said segment connector and said stopper retention cap on said rigid stopper coupling, wherein said segment connector has a segment outside diameter less than said cap outside diameter such that said stopper retention ledge extends between a cap outer edge of said stopper retention cap bounding said cap outside diameter and a segment outer edge of said connector segment bounding said segment outside diameter;
releasably attaching a plunger retention bracket of a plunger coupling to a first end of a syringe plunger, wherein said plunger retention bracket is an arcuate wall having a horseshoe-shaped configuration partially extending around an interior void space within said plunger retention bracket accessible from outside said plunger retention bracket through an opening in said arcuate wall, wherein said plunger retention bracket is selectively attached to said first end of said syringe plunger by press-fitting said first end of said syringe plunger through said opening into said interior void space and retaining said first end of said syringe plunger in said interior void space and is selectively detached from the first end of said syringe plunger by withdrawing the syringe plunger through said opening out of said interior void space;
releasably attaching said plunger coupling to said rigid stopper coupling; and
inserting said elastic syringe stopper, said rigid stopper coupling, said plunger coupling and said first end of said syringe plunger into an interior of a syringe barrel enclosed by a barrel sidewall via a first end of said syringe barrel, wherein said arcuate wall of said plunger retention bracket is parallely aligned with said barrel sidewall, wherein said first end, said barrel sidewall and a second end of said syringe barrel bound said interior of said syringe barrel, and wherein said elastic syringe stopper in cooperation with said rigid stopper coupling seals a sealed portion of said interior of said syringe barrel between said elastic syringe stopper and said second end of said syringe barrel from the external environment of said syringe barrel.

17. The method of claim 16 further comprising the steps of:
  detaching said plunger coupling from said rigid stopper coupling while said rigid stopper coupling is in said interior of said syringe barrel;
  withdrawing said plunger coupling and said syringe plunger in their entirety from said syringe barrel while maintaining said elastic syringe stopper and said rigid stopper coupling attached thereto in said syringe barrel such that said syringe barrel with said elastic syringe stopper and said rigid stopper coupling therein comprises a fluid reservoir, wherein said fluid reservoir maintains said sealed portion of said interior of said syringe barrel.

18. The method of claim 17, wherein said fluid reservoir is used as a sealed centrifuge container that holds a fluid while said fluid is being centrifuged.

19. The syringe sealing assembly of claim 7, wherein said plunger retention bracket has a circumferential slot on an inside face of said arcuate wall, wherein said circumferential slot is adaptable to receive a disk-configured member of the syringe plunger perpendicularly aligned with said arcuate wall when the syringe plunger is retained in said interior void space, thereby facilitating selective attachment of said plunger retention bracket to the syringe plunger.

20. The method of claim 16, wherein said plunger retention bracket has a circumferential slot on an inside face of said arcuate wall, wherein said circumferential slot receives a disk-configured member of said syringe plunger perpendicularly aligned with said arcuate wall when said syringe plunger is retained in said interior void space.

* * * * *